United States Patent
Shi et al.

(10) Patent No.: US 9,168,140 B2
(45) Date of Patent: Oct. 27, 2015

(54) PERFORATED OSTEOCHONDRAL ALLOGRAFT COMPOSITIONS

(71) Applicant: AlloSource, Centennial, CO (US)

(72) Inventors: Yaling Shi, Larkspur, CO (US); Carolyn Barrett, Denver, CO (US)

(73) Assignee: AlloSource, Centennial, CO (US)

( * ) Notice: Subject to any disclaimer, the term of this patent is extended or adjusted under 35 U.S.C. 154(b) by 0 days.

(21) Appl. No.: 14/210,111

(22) Filed: Mar. 13, 2014

(65) Prior Publication Data

US 2014/0271570 A1    Sep. 18, 2014

Related U.S. Application Data

(60) Provisional application No. 61/792,074, filed on Mar. 15, 2013.

(51) Int. Cl.
*A61F 2/28* (2006.01)
*A61F 2/30* (2006.01)

(52) U.S. Cl.
CPC .............. *A61F 2/30756* (2013.01); *A61F 2/28* (2013.01); *A61F 2/3094* (2013.01); *A61F 2002/30784* (2013.01); *A61F 2002/30827* (2013.01)

(58) Field of Classification Search
USPC .................. 424/93.7, 423; 623/23.3, 23.63
See application file for complete search history.

(56) References Cited

U.S. PATENT DOCUMENTS

| | | | |
|---|---|---|---|
| 4,932,973 A * | 6/1990 | Gendler | 623/23.63 |
| 5,582,752 A | 12/1996 | Zair | |
| 6,050,991 A | 4/2000 | Guillet | |
| 6,607,524 B1 | 8/2003 | LaBudde et al. | |
| 6,638,271 B2 | 10/2003 | Munnerlyn et al. | |
| 6,712,822 B2 | 3/2004 | Re et al. | |
| 6,858,042 B2 | 2/2005 | Nadler et al. | |
| 7,361,195 B2 | 4/2008 | Schwartz et al. | |
| 7,550,007 B2 | 6/2009 | Malinin | |
| 7,758,643 B2 | 7/2010 | Stone et al. | |
| 7,824,711 B2 | 11/2010 | Kizer et al. | |
| 7,838,040 B2 | 11/2010 | Malinin | |
| 7,875,296 B2 | 1/2011 | Binette et al. | |
| RE42,208 E | 3/2011 | Truncale et al. | |
| 7,931,692 B2 | 4/2011 | Sybert et al. | |
| 8,012,206 B2 | 9/2011 | Schmieding | |
| 8,043,450 B2 | 10/2011 | Cali et al. | |
| 8,142,502 B2 | 3/2012 | Stone et al. | |
| 8,173,162 B2 | 5/2012 | Vilei et al. | |
| 8,221,500 B2 | 7/2012 | Truncale et al. | |
| 8,318,212 B2 | 11/2012 | Malinin | |
| 8,435,551 B2 | 5/2013 | Semler et al. | |
| 8,497,121 B2 | 7/2013 | Yao et al. | |
| 8,641,775 B2 | 2/2014 | Harmon et al. | |
| 8,652,214 B2 | 2/2014 | Fritz et al. | |
| 8,652,507 B2 | 2/2014 | Kizer et al. | |
| 8,883,210 B1 | 11/2014 | Truncale et al. | |
| 8,945,535 B2 | 2/2015 | Steinwachs et al. | |
| 2003/0229400 A1 * | 12/2003 | Masuda et al. | 623/23.63 |
| 2004/0078090 A1 | 4/2004 | Binette et al. | |
| 2006/0275273 A1 | 12/2006 | Seyedin et al. | |
| 2007/0265705 A1 | 11/2007 | Gaissmaier et al. | |
| 2007/0276506 A1 * | 11/2007 | Troxel | 623/23.63 |
| 2007/0299517 A1 | 12/2007 | Davisson et al. | |
| 2008/0160496 A1 | 7/2008 | Rzepakovsky et al. | |
| 2008/0269895 A1 | 10/2008 | Steinwachs et al. | |
| 2009/0024223 A1 | 1/2009 | Chen et al. | |
| 2010/0049322 A1 | 2/2010 | McKay | |
| 2010/0124776 A1 | 5/2010 | Shi | |
| 2010/0274362 A1 | 10/2010 | Yayon et al. | |
| 2011/0045044 A1 | 2/2011 | Masinaei et al. | |
| 2011/0091517 A1 | 4/2011 | Binette et al. | |
| 2011/0177134 A1 | 7/2011 | Harmon et al. | |
| 2011/0182961 A1 | 7/2011 | McKay | |
| 2011/0196355 A1 | 8/2011 | Mitchell et al. | |
| 2011/0274729 A1 | 11/2011 | Collins | |
| 2012/0107384 A1 | 5/2012 | Yao et al. | |
| 2013/0030528 A1 | 1/2013 | Chen et al. | |
| 2013/0035676 A1 | 2/2013 | Mitchell et al. | |
| 2013/0122095 A1 | 5/2013 | Kestler et al. | |
| 2013/0197654 A1 | 8/2013 | Samuelson et al. | |
| 2013/0204392 A1 | 8/2013 | Law et al. | |
| 2013/0344114 A1 | 12/2013 | Chang et al. | |
| 2014/0012393 A1 | 1/2014 | Shin et al. | |
| 2014/0017283 A1 | 1/2014 | Yoo et al. | |
| 2014/0017292 A1 | 1/2014 | Yoo et al. | |
| 2014/0024115 A1 | 1/2014 | Bogdansky et al. | |
| 2014/0030309 A1 | 1/2014 | Yoo et al. | |
| 2014/0039621 A1 | 2/2014 | Gordon et al. | |
| 2014/0058527 A1 | 2/2014 | Truncale et al. | |
| 2014/0134212 A1 | 5/2014 | Shi et al. | |
| 2014/0222159 A1 | 8/2014 | Bursac et al. | |
| 2014/0255506 A1 | 9/2014 | Behnam et al. | |
| 2015/0004211 A1 | 1/2015 | Yoo et al. | |
| 2015/0017222 A1 | 1/2015 | Yoo et al. | |
| 2015/0140057 A1 | 5/2015 | Yoo et al. | |

FOREIGN PATENT DOCUMENTS

WO    WO/2005/058207    6/2005

OTHER PUBLICATIONS

Outerbridge, RE, "The Etiology of Chondromalacia Patellae," J Bone Joint Surg Br, 43:752-757 (1961).

(Continued)

*Primary Examiner* — Ralph Gitomer

(74) *Attorney, Agent, or Firm* — Kilpatrick Townsend & Stockton LLP

(57) ABSTRACT

Osteochondral graft composition comprising a cartilage component and a bone component, and further comprising one or more perforations in the bone component and/or the cartilage component, are provided. Methods of manufacturing and using osteochondral graft compositions comprising one or more perforations in the bone component and/or the cartilage component are also provided.

27 Claims, 5 Drawing Sheets

(56) References Cited

OTHER PUBLICATIONS

Mour, et al. "Advances in Porus Biomaterials for Dental and Orthopaedic Applications," Materials www.mdpi.com/journal/materials published Apr. 2010, 28 pages.

Peterson, et al. "Osteoinductivity of Commercially Available Demineralized Bone Matrix," The Journal of Bone and Joint Surgery, Incorporated. Published 2004, 8 pages.

Petrochenko, et al. "Novel Approaches to Bone Grafting: Porosity, Bone Morphogenetic Proteins, Stem Cells, and the Periosteum," National Institutes of Health Public Access, published 2010, 14 pages.

Albrecht, F., et al. "Closure of Osteochondral Lesions Using Chondral Fragments and Fibrin Adhesive." Archives of Orthopaedic and Traumatic Surgery, vol. 101 (1983): pp. 213-217.

Allosource. (Sep. 2012). "DeNovo® NT: Natural Tissue Graft" [Brochure]. Centennial, CO. AlloSource. 2 pages.

Farr, J., et al. "Chondral defect repair with particulated juvenile cartilage allograft." Electronic Poster. *International Cartilage Repair Society*, Sep. 26-29, 2010, Sitges/Barcelona, Spain. Retrieved from <http://posters.webges.com/icrs/epos> on Oct. 11, 2010. 14 pages.

Eyre, D. Collagen of articular cartilage, Arthritis Res. 4:30-35 (2002).

Frisbie, D. D., et al. "In Vivo Evaluation of a One Step Autologous Cartilage Resurfacing Technique in a Long Term Equine Model." Poster #1355. $51^{st}$ Annual Meeting of the Orthopaedic Research Society, May 20-23, 2005. One page.

Lu, Y., et al., "Minced Cartilage without Cell Culture Serves as an Effective Intraoperative Cell Source for Cartilage Repair." *Journal of Orthopaedic Research* (Jun. 2006): pp. 1261-1270.

Stone, K. R., et al. "Articular Cartilage Paste Grafting to Full-Thickness Articular Cartilage Knee Joint Lesions: A 2-to 12-Year Follow-up." *Arthroscopy: The Journal of Arthroscopc and Related Surgery*, vol. 22, No. 3 (Mar. 2006): pp. 291-299.

Zimmer, "Articular Cartilage Repair: Basic Science." *Zimmer Technical Memo.* (2009) Zimmer, Inc. 3 pages.

\* cited by examiner

FIG. 6B-C

PERFORATED OSTEOCHONDRAL ALLOGRAFT COMPOSITIONS

CROSS-REFERENCE TO RELATED APPLICATIONS

This application claims benefit of priority of U.S. Provisional Application No. 61/792,074, filed Mar. 15, 2013, the entire content of which is incorporated herein by reference.

BACKGROUND OF THE INVENTION

Cartilage tissue can be found throughout the human anatomy. The cells within cartilage tissue are called chondrocytes. These cells generate proteins (e.g., collagen, proteoglycan, and elastin) that are involved in the formation and maintenance of the cartilage. Hyaline cartilage is present on certain bone surfaces, where it is commonly referred to as articular cartilage. Such cartilage contains significant amounts of collagen (e.g., two-thirds of the dry weight), and cross-linking of the collagen imparts a high material strength and firmness to the tissue. These mechanical properties are important to the proper performance of the articular cartilage within the body.

Osteochondral allografting ("OATS") is a desirable treatment option to repair large articular defects, providing functional restoration of the affected joint. Traditionally, osteochondral allografts are implanted fresh, within 7 days, and have high chondrocyte viability at implantation. Microfracture surgery is an articular cartilage repair surgical technique that works by creating tiny holes, or fractures, in the bone underlying the cartilage. Blood and bone marrow flow into the damaged area to form a "super-clot", from which new cartilage develops. However, this technique has several limitations, including lack of efficacy for large and deep osteochondral defects, limited availability, non-filled spaces between the circular grafts, and incomplete integration of the donor and recipient cartilage.

BRIEF SUMMARY OF THE INVENTION

In one aspect, perforated osteochondral graft compositions are provided. In some embodiments, the perforated osteochondral graft composition comprises: a continuous portion of an osteochondral tissue, wherein the continuous portion of osteochondral tissue comprises a cartilage component and a bone component, and wherein the osteochondral graft composition comprises one or more perforations in the cartilage component and/or the bone component.

In some embodiments, the osteochondral tissue is harvested from a human cadaveric donor.

In some embodiments, the one or more perforations have an average diameter from about 100 µm to about 3 mm. In some embodiments, the one or more perforations extend entirely through the depth of the continuous portion of osteochondral tissue. In some embodiments, the one or more perforations extend partially through the depth of the continuous portion of osteochondral tissue.

In some embodiments, at least a portion of the surface of the perforated osteochondral graft composition is coated with a biological adhesive. In some embodiments, at least a portion of the surface of the perforated osteochondral graft composition is seeded with stem cells.

In another aspect, methods of treating a cartilage or bone defect in a subject are provided. In some embodiments, the method comprising administering to the subject a perforated osteochondral graft composition as described herein. In some embodiments, the subject has a full-thickness or nearly full-thickness cartilage defect. In some embodiments, the subject has a Grade 3 or Grade 4 articular cartilage lesion.

In another aspect, kits for treating a cartilage or bone defect in a subject are provided. In some embodiments, the kit comprises a perforated osteochondral graft composition as described herein in a biocompatible medium. In some embodiments, the biocompatible medium comprises a growth medium. In some embodiments, the biocompatible carrier (e.g., growth medium) comprises one or more antibiotics.

In still another aspect, methods of manufacturing a perforated osteochondral graft composition are provided. In some embodiments, the method comprises:

obtaining a continuous portion of an osteochondral tissue from a human cadaveric donor, wherein the continuous portion of osteochondral tissue comprises a bone component and a cartilage component; and cutting one or more perforations into the bone component and/or the cartilage component of the osteochondral tissue.

In some embodiments, the cutting step comprises cutting the osteochondral tissue with a laser cutter, with a mechanical blade, or with a mechanical press. In some embodiments, the cutting step comprises cutting the osteochondral tissue with a laser cutter. In some embodiments, the cutting step comprises cutting the osteochondral tissue with the laser cutter at a speed from about 5% to about 15%, a power from about 35% to about 100%, and a frequency from about 1500 Hz to about 5000 Hz.

In some embodiments, the one or more perforations that are cut into the osteochondral tissue extend entirely through the depth of the continuous portion of osteochondral tissue. In some embodiments, the one or more perforations that are cut into the osteochondral tissue extend partially through the depth of the continuous portion of osteochondral tissue. In some embodiments, the one or more perforations have an average diameter from about 100 µm to about 3 mm.

In some embodiments, following the cutting step, the method further comprises coating at least a portion of the osteochondral graft with a biological adhesive. In some embodiments, following the cutting step, the method further comprises seeding stem cells onto at least a portion of the osteochondral graft.

In some embodiments, following the cutting step, the method further comprises suspending the osteochondral graft in a biocompatible medium.

DETAILED DESCRIPTION OF THE INVENTION

I. Introduction

Figure 1:
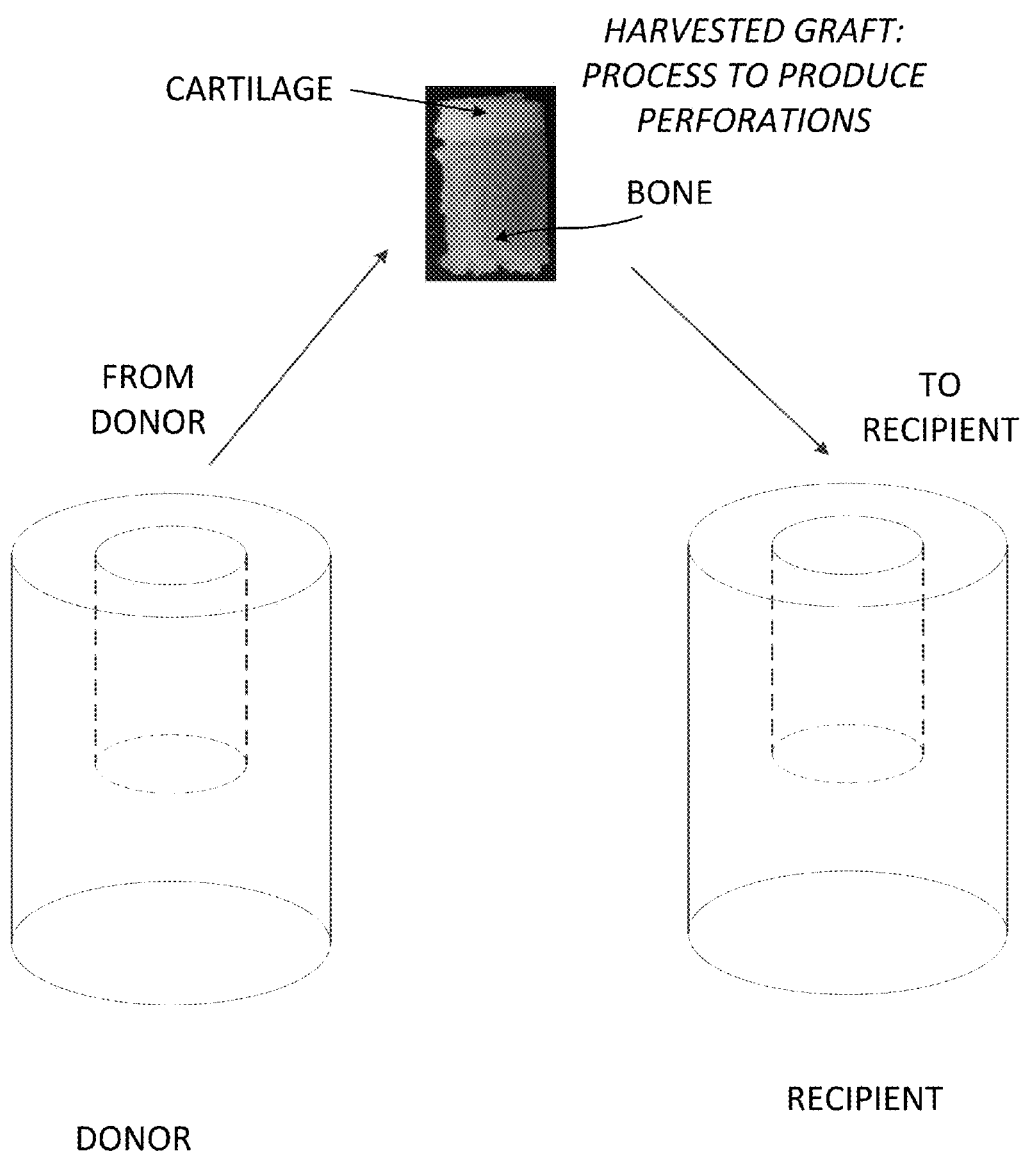
FIG. 1. An osteochondral graft having a cartilage component and a bone component (e.g., a graft that is cylindrical in shape) can be harvested from a cadaveric donor. The graft assembly can be processed as described herein to produce perforations in the graft. The perforated graft can then be implanted in the recipient patient.

In one aspect, the present application relates to osteochondral allografts comprising a bone component and a cartilage component, and comprising one or more perforations in the bone component and/or cartilage component of the osteochondral allograft. Without being bound to a particular theory, it is believed that the presence of perforations in an osteochondral allograft enhances cell migration and transfusion of nutrients from the allograft into a treatment site, resulting in an improved clinical outcome, such as faster healing of a defect (e.g., cartilage or bone defect) as compared to an osteochondral allograft lacking perforations. The osteochondral allografts described herein can be prepared or utilized for any type of tissue that is dense and/or hard to heal, including but not limited to cartilage, tendon, cortical bone, etc.

In some embodiments, the osteochondral graft compositions described herein can be used to treat medium to large articular cartilage lesions, complex or multiple cartilage lesions, or subjects with bone loss. In contrast, cartilage repair techniques (e.g., using cartilage grafts which lack a bone component) are not suitable for treating larger or more complex lesions or for treating bone loss.

II. Perforated Osteochondral Graft Compositions

In one aspect, perforated osteochondral graft compositions are provided. In some embodiments, the composition comprises a continuous portion of an osteochondral tissue, wherein the continuous portion of osteochondral tissue comprises a bone component and a cartilage component, and wherein the osteochondral graft composition comprises one or more perforations in the bone component and/or the cartilage component. As used herein, the term "continuous portion of an osteochondral tissue" refers to a single sheet or piece of osteochondral tissue comprising both cartilage tissue and bone tissue within the single sheet or piece. As a non-limiting example, in some embodiments, a continuous portion of an osteochondral tissue is a piece of osteochondral tissue harvested from a humeral head or a femoral condyle.

The osteochondral graft can comprise any osteochondral tissue. For example, the osteochondral graft can comprise osteochondral tissue from the humerus (e.g., humeral head), femur (e.g., femoral condyle), tibia, ilium, fibula, radius, ulna, trochlea, patella, talus, or ankle The osteochondral graft can have any suitable shape. For example, the osteochondral graft can have a cylinder or "dowel" shape, a cube or rectangular shape, or an irregular shape. In some embodiments, the osteochondral graft comprises a cylindrical or dowel shape. See, e.g., FIG. 1. In some embodiments, the osteochondral graft has a diameter of about 10 mm, about 11 mm, about 12 mm, about 13 mm, about 14 mm, about 15 mm, about 16 mm, about 17 mm, about 18 mm, about 19 mm, or about 20 mm. In some embodiments, the osteochondral graft has a length of about 10 mm, about 15 mm, about 20 mm, about 25 mm, or about 30 mm.

In some embodiments, the osteochondral tissue is obtained from a cadaveric donor. In some embodiments, the donor is an adult cadaveric donor that is 18 years of age or older at the time of the donation. In some embodiments, the donor is an adult cadaveric donor that is between the ages of 15 and 45 at the time of the donation. In some embodiments, the osteochondral tissue is from a human juvenile cadaveric donor. In some embodiments, the donor is a juvenile cadaveric donor that is between the ages of 3 and 12 at the time of the donation.

Perforations

In some embodiments, the osteochondral allograft compositions comprise 1, 2, 3, 4, 5, 6, 7, 8, 9, 10, 15, 20, 25, 30, 35, 40, 45, 50, 60, 70, 80, 90, 100, 150, 200 or more perforations in the osteochondral tissue. In some embodiments, the one or more perforations have an average diameter that is about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1 mm, about 1.5 mm, about 2 mm, about 2.5 mm, or about 3 mm. In some embodiments, the one or more perforations have an average diameter from about 100 µm to about 3 mm. In some embodiments, the one or more perforations have an average diameter from about 100 µm to about 2 mm. In some embodiments, the one or more perforations have an average diameter that is from about 100 µm to about 1000 µm. In some embodiments, the one or more perforations have an average diameter that is from about 100 µm to about 500 µm. In some embodiments, the one or more perforations have an average diameter than is less than about 200 µm, e.g., about 175 µm, about 150 µm, about 125 µm, about 100 µm or less. In some embodiments, the one or more perforations have an average diameter that is from about 0.5 mm to about 3 mm, from about 0.5 mm to about 2 mm, or from about 0.5 mm to about 1 mm. In some embodiments, the osteochondral allograft composition comprises a plurality of perforations, and the perforations vary in their average diameter. For example, the osteochondral allograft composition can have two, three, four, or more sizes of perforations.

In some embodiments, the osteochondral allograft composition comprises a plurality of perforations that are cut into the osteochondral tissue in such a way as to form a line or lines in the osteochondral tissue. As a non-limiting example, a series of perforations (e.g., microperforations) can be cut into the osteochondral tissue to form a circle or ring shape within the osteochondral graft. See, FIG. 5. As another non-limiting example, a series of perforations (e.g., microperforations) can be cut into the osteochondral tissue to form a grid shape within the osteochondral graft. See, FIG. 6. The perforations forming the line or lines (e.g., forming a circle or grid shape) can extend partially or entirely through the depth of the osteochondral tissue.

In some embodiments, the osteochondral allograft composition comprises one or more perforations that extend partially through the depth of the osteochondral tissue. For example, in some embodiments, one or more perforations extend partially through the cartilage component and does not extend into the bone component. In some embodiments, the one or more perforations extend entirely through the depth of the cartilage component but do not extend into the bone component. In some embodiments, the one or more perforations extend entirely through the depth of the cartilage component and extend partially through the depth of the bone component. In some embodiments, the one or more perforations extend entirely through the depth of both the cartilage component and the bone component.

In some embodiments, the osteochondral allograft composition comprises a plurality of perforations, and the perforations vary in their depth through the osteochondral tissue. For example, in some embodiments, the composition comprises at least one perforation that extends entirely through the osteochondral tissue (i.e., entirely through the depth of the cartilage component and the bone component), and at least one perforation that only extends partially through the osteochondral tissue (e.g., extends partially through the cartilage component, extends entirely through the cartilage component but does not extend into the bone component, or extends entirely through the cartilage component and extends partially into the bone component).

In some embodiments, the perforated osteochondral allograft composition further comprises a biocompatible medium in which the osteochondral allograft is stored. In some embodiments, the biocompatible medium comprises a growth medium. Suitable examples of growth medium include, but are not limited to, Dulbecco's Modified Eagle's Medium (DMEM) with 5% Fetal Bovine Serum (FBS). In some embodiments, growth medium includes a high glucose DMEM. In some embodiments, the biocompatible carrier (e.g., growth medium) comprises one or more antibiotics.

In some embodiments, the biocompatible medium comprises a cryopreservation medium. In some embodiments, the biocompatible medium comprises one or more cryoprotective agents such as, but not limited to, glycerol, DMSO, hydroxyethyl starch, polyethylene glycol, propanediol, ethylene glycol, butanediol, polyvinylpyrrolidone, or alginate.

Additional Biological Components

In some embodiments, the perforated osteochondral allograft composition is combined with one or more other biological components. For example, in some embodiments, at least a portion of the osteochondral allograft composition is coated with a biological adhesive. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, basement membrane matrix (e.g., MATRIGEL®, BD Biosciences, San Jose, Calif.), laminin, elastin, proteoglycans, autologous glue, and combinations thereof.

In some embodiments, at least a portion of the perforated osteochondral allograft composition is combined with cells such as stem cells. For example, in some embodiments, the osteochondral allograft composition is seeded with stem cells, such as mesenchymal stem cells. Mesenchymal stem cells can be obtained from a variety of tissues, including but not limited to bone marrow tissue, adipose tissue, muscle tissue, birth tissue (e.g., amnion, amniotic fluid, or umbilical cord tissue), skin tissue, bone tissue, and dental tissue. In some embodiments, the mesenchymal stem cells are derived from a tissue (e.g., adipose tissue) that has been processed (i.e., digested) to form a cell suspension comprising mesenchymal stem cells and non-mesenchymal stem cells that is seeded onto the osteochondral allograft, and wherein the mesenchymal stem cells are not cultured ex vivo (e.g., on a plastic dish) prior to seeding the cell suspension on the osteochondral allograft. Stem cell-seeded bone and cartilage substrates and methods of preparing such substrates are described in published application US 2010/0124776 and in U.S. application Ser. No. 12/965,335, the contents of each of which are incorporated by reference herein.

In some embodiments, at least a portion of the osteochondral allograft composition is combined with one or more growth factors. Suitable growth factors include, but are not limited to, transforming growth factor-beta (TGFβ), fibroblast growth factor (FGF) (e.g., FGF2, FGF5), bone morphogenetic protein (BMP) (e.g., BMP2, BMP4, BMP6, BMP7), platelet derived growth factor (PDGF), and insulin-related growth factor (IGF) (e.g., IGF1, IGF2).

In some embodiments, the osteochondral allograft composition is at least partially coated with a biological adhesive prior to adding the one or more growth factors and/or seeding the cells (e.g., mesenchymal stem cells) on the osteochondral allograft.

In some embodiments, the perforated osteochondral allograft composition is combined with one or more growth factors.

III. Methods of Manufacturing Perforated Osteochondral Graft Compositions

In another aspect, methods of manufacturing perforated osteochondral allograft compositions are provided. In some embodiments, the method comprises:

obtaining a continuous portion of an osteochondral tissue from a human cadaveric donor, wherein the continuous portion of osteochondral tissue comprises a bone component and a cartilage component; and cutting one or more perforations into the bone component and/or the cartilage component.

In some embodiments, the osteochondral tissue is harvested from an adult cadaveric donor. In some embodiments, the osteochondral tissue is harvested from an adult cadaveric donor that is between the ages of 15 and 45 at the time of the donation. In some embodiments, the osteochondral tissue is harvested from a juvenile cadaveric donor.

The perforation techniques can be used with any size of graft tissue piece or construct, and may be used with any of a variety of osteochondral tissues. In some embodiments, the graft comprises osteochondral tissue from the humerus (e.g., humeral head), femur (e.g., femoral condyle), tibia, ilium, fibula, radius, ulna, trochlea, patella, talus, or ankle. In some embodiments, the graft comprises a cylinder or "dowel" shape, a cube or rectangular shape, or an irregular shape.

Perforations can include, for example, microperforations, bores, apertures, and the like. In some embodiments, perforations may be on the order of tens of microns in dimension, or less. In some embodiments, perforations may be on the order of millimeters in dimension, or less. For example, in some embodiments, the perforations have an average diameter of about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1 mm, about 1.5 mm, about 2 mm, about 2.5 mm, or about 3 mm. In some embodiments, perforation techniques can involve the formation of holes having a diameter of about 0.10 mm, or smaller. In some embodiments, 1, 2, 3, 4, 5, 6, 7, 8, 9, 10, 15, 20, 25, 30, 35, 40, 45, 50, 60, 70, 80, 90, 100, 150, 200 or more perforations are cut into the osteochondral tissue.

In some embodiments, the osteochondral tissue is cut using a cutting mechanism. In some embodiments, the cutting mechanism is a laser cutting apparatus, a mechanical blade, a manual cutting apparatus, a manual pressing apparatus, or the like. In some embodiments, the cutting mechanism comprises a pneumatic press, such as an air press or an oil press, or a screw press.

In some embodiments, the osteochondral tissue is cut using a laser cutting apparatus. For example, in some embodiments, the laser cutting apparatus is a laser engraver. Non-limiting examples of suitable engraving lasers include $CO_2$ engraving lasers, such as the Epilog Zing 30 Watt $CO_2$ engraving laser. In some embodiments, the cutting step comprises cutting the cartilage tissue with the laser cutting apparatus at a speed from about 5% to about 15% (e.g., about 5%, about 6%, about 7%, about 8%, about 9%, about 10%, about 11%, about 12%, about 13%, about 14%, or about 15%), at a power of about 35% to about 100% (e.g., about 35%, about 40%, about 45%, about 50%, about 55%, about 60%, about 65%, about 70%, about 75%, about 80%, about 85%, about 90%, about 95%, or about 100%), and a frequency of about 1500 Hz to about 5000 Hz (e.g., about 1500 Hz, about 1600 Hz, about 1700 Hz, about 1800 Hz, about 1900 Hz, about 2000 Hz, about 2100 Hz, about 2200 Hz, about 2300 Hz, about 2400 Hz, about 2500 Hz, about 2600 Hz, about 2700 Hz, about 2800 Hz, about 2900 Hz, about 3000 Hz, about 3100 Hz, about 3200 Hz, about 3300 Hz, about 3400 Hz, about 3500 Hz, about 3600 Hz, about 3700 Hz, about 3800 Hz, about 3900 Hz, about 4000 Hz, about 4100 Hz, about 4200 Hz, about 4300 Hz, about 4400 Hz, about 4500 Hz, about 4600 Hz, about 4700 Hz, about 4800 Hz, about 4900 Hz, or about 5000 Hz). Suitable speeds, powers, and frequencies for cutting the cartilage tissue are shown in Table 1. In some embodiments, the cutting step comprises cutting the cartilage tissue with the laser cutting apparatus at a speed of about 10%, a power of about 100%, and a frequency of about 5000 Hz. In some embodiments, the cutting step comprises cutting the cartilage tissue with the laser cutting apparatus at a speed of about 5%, a power of about 100%, and a frequency of about 5000 Hz. In some embodiments, the cutting step comprises cutting the cartilage tissue with the laser cutting apparatus at a speed of about 10%, a power of about 65%, and a frequency of about 4000 Hz. In some embodiments, the cutting step comprises cutting the cartilage tissue with the laser cutting apparatus at a speed of about 15%, a power of about 35%, and a frequency of about 1500 Hz.

The perforation techniques disclosed herein, such as the laser perforation modalities, can operate without subjecting the tissue to undue pressure which would otherwise cause the tissue to deform, tear, or otherwise become distorted. Laser perforation techniques can efficiently ablate the tissue, and leave a clean and intact hole without distorting the tissue. It has been found that the laser does not burn the cells as it bores through the material. Rather, the cells remain viable and are observed to grow out of or passage through the perforated tissue.

In some embodiments, prior to the cutting step, the osteochondral allograft is washed with a saline solution.

In some embodiments, following the cutting step, the perforated osteochondral allograft is suspended in a biocompatible medium. In some embodiments, the biocompatible medium comprises a growth medium. Suitable examples of growth medium include, but are not limited to, Dulbecco's Modified Eagle's Medium (DMEM) with 5% Fetal Bovine Serum (FBS). In some embodiments, growth medium includes a high glucose DMEM. In some embodiments, the biocompatible carrier (e.g., growth medium) comprises one or more antibiotics. In some embodiments, the biocompatible medium comprises a cryopreservation medium. In some embodiments, the biocompatible medium comprises one or more cryoprotective agents such as, but not limited to, glycerol, DMSO, hydroxyethyl starch, polyethylene glycol, propanediol, ethylene glycol, butanediol, polyvinylpyrrolidone, or alginate.

In some embodiments, the perforated osteochondral allograft is not subjected to an additional processing step prior to suspending the osteochondral allograft in the biocompatible medium. In some embodiments, following the cutting step, the osteochondral allograft can be subjected to one or more additional processing steps prior to suspending the osteochondral allograft in the biocompatible medium. In some embodiments, the osteochondral allograft is washed with a saline solution. In some embodiments, the osteochondral allograft is treated with one or more enzymes that promote the release of chondrocyte cells from cartilage matrix in the osteochondral allograft. For example, collagenase can be applied to help release chondrocyte cells from the cartilage matrix in the osteochondral allograft. In some embodiments, the osteochondral allograft is not enzymatically digested, such as with a collagenase.

In some embodiments, following the cutting step, at least a portion of the osteochondral allograft composition is coated with a biological adhesive. Suitable biological adhesives include, but are not limited to, fibrin, fibrinogen, thrombin, fibrin glue (e.g., TISSEEL), polysaccharide gel, cyanoacrylate glue, gelatin-resorcin-formalin adhesive, collagen gel, synthetic acrylate-based adhesive, cellulose-based adhesive, basement membrane matrix (e.g., MATRIGEL®, BD Biosciences, San Jose, Calif.), laminin, elastin, proteoglycans, autologous glue, and combinations thereof.

In some embodiments, following the cutting step, at least a portion of the perforated osteochondral allograft composition is combined with one or more growth factors. Suitable growth factors include, but are not limited to, transforming growth factor-beta (TGFβ), fibroblast growth factor (FGF) (e.g., FGF2, FGF5), bone morphogenetic protein (BMP) (e.g., BMP2, BMP4, BMP6, BMP7), platelet derived growth factor (PDGF), and insulin-related growth factor (IGF) (e.g., IGF1, IGF2).

In some embodiments, following the cutting step, at least a portion of the perforated osteochondral allograft composition is combined with cells such as stem cells. For example, in some embodiments, the osteochondral allograft composition is seeded with stem cells, such as mesenchymal stem cells. In some embodiments, the method further comprises: digesting a tissue (e.g., adipose tissue) to form a cell suspension comprising mesenchymal stem cells and non-mesenchymal stem cells; seeding the cell suspension onto the osteochondral allograft, wherein the mesenchymal stem cells are not cultured ex vivo (e.g., on a plastic dish) prior to seeding the cell suspension on the osteochondral allograft. Methods of preparing such substrates are described in published application US 2010/0124776 and in U.S. application Ser. No. 12/965, 335, the contents of each of which are incorporated by reference herein.

In some embodiments, following the cutting step, at least a portion of the osteochondral allograft composition is with a biological adhesive (e.g., fibrin glue) prior to adding the one or more growth factors and/or seeding the cells (e.g., mesenchymal stem cells) on the osteochondral allograft. In some embodiments, the cells to be seeded (e.g., mesenchymal stem cells) are combined with the biological adhesive (e.g., fibrin glue) prior to seeding the cells on the osteochondral allograft.

IV. Therapeutic Uses of Perforated Osteochondral Graft Compositions

In another aspect, a perforated osteochondral graft composition as described herein can be used to treat bone and cartilage defects in a subject. Without being bound to a particular theory, it is believed that perforations (e.g., holes or microperforations) in the osteochondral tissue can operate to enhance cell migration and nutrient transfusion throughout the graft and implant treatment area, in order to achieve an improved clinical outcome. These tissue treatment techniques can be applied to any tissue type which is dense and hard to heal, such as cortical bone, cartilage, tendon, and the like. Thus, the osteochondral grafts described herein can be used to treat large and deep osteochondral defects, and to prevent or inhibit the presence of non-filled spaces between circular grafts and incomplete integration of the donor and recipient cartilage. Additionally, the osteochondral grafts described herein preserve the natural biomechanical characteristics of the osteochondral product. By keeping the native characteristics of the allograft (e.g., biomechanical properties and natural osteoinductive and cartilaginous growth factors present in the osteochondral graft), administration of the perforated osteochondral graft results in a better chance of successful incorporation and defect repair, for example as compared to a more flexible allograft or a graft lacking a bone component.

In some embodiments, a perforated osteochondral graft composition as described herein (e.g., a composition comprising a continuous portion of an osteochondral tissue, wherein the continuous portion of osteochondral tissue comprises a cartilage component and a bone component, and wherein the osteochondral graft composition comprises one or more perforations in the cartilage component and/or the bone component) is administered to a patient to treat an osteochondral defect or injury in the patient recipient. In some embodiments, the perforated osteochondral graft composition is administered at a site of defect or injury in cartilage, bone, ligament, tendon, meniscus, or joint. In some embodiments, the defect is a large or deep osteochondral defect (e.g., at a joint, e.g., a knee joint). In some embodiments, the subject has osteoarthritis. In some embodiments, the subject has a degenerative osteochondral defect or injury.

In some embodiments, a perforated osteochondral graft composition as described herein is used to treat a subject having a full-thickness or nearly full-thickness cartilage defect. The Outerbridge classification of articular cartilage injuries is the most widely used to describe the size of a cartilage lesion. See, Outerbridge R E, *J Bone Joint Surg Br* 43:752-757 (1961). This classification provides a distinction between a partial (Grades 1 and 2) versus nearly full or full-thickness cartilage defect (Grades 3 and 4); between a small (Grade 2) and larger (Grade 3) lesion; and describes a complete loss of cartilage (Grade 4). Osteochondral grafts, such as the perforated graft compositions described herein, are particularly suitable for treating nearly full or full-thickness cartilage defects (Grades 3 and 4) and medium to large (Grade 3) articular cartilage lesions. Osteochondral grafts, such as the perforated graft compositions described herein, are also particularly suitable for treating osteochondritis dissecans, focal chondral defects >2-3 $cm^2$ in femoral condyles or patellofemoral defects, or for treatments in which there is misalignment, meniscal deficiency, or ligament insufficiency.

In some embodiments, a perforated osteochondral graft composition as described herein is administered locally to the subject. In some embodiments, the perforated osteochondral graft composition is implanted in the subject. In some embodiments, the perforated osteochondral graft composition is administered in a minimally invasive procedure, e.g., arthroscopy. In some embodiments, perforated osteochondral graft composition is administered by osteochondral allograft transplantation surgery (OATS).

In some embodiments, a perforated osteochondral graft composition as described herein is administered (e.g., implanted) "fresh," i.e., within 7 days of harvesting the osteochondral tissue. Such fresh osteochondral graft compositions are believed to have a high amount of chondrocyte viability at the time of administration.

In some embodiments, a perforated osteochondral graft composition as described herein can be shaped into a smaller piece by the user (e.g., surgeon) to an appropriate size to suit the size of the defect being treated.

V. Kits

In still another aspect, kits comprising a perforated osteochondral graft composition as described herein are provided. In some embodiments, the kit comprises a perforated osteochondral graft composition comprising a continuous portion of an osteochondral tissue, wherein the continuous portion of osteochondral tissue comprises a cartilage component and a bone component, and wherein the osteochondral graft composition comprises one or more perforations in the cartilage component and/or the bone component; and a biocompatible medium.

In some embodiments, the biocompatible medium comprises a growth medium. Suitable examples of growth medium include, but are not limited to, Dulbecco's Modified Eagle's Medium (DMEM) with 5% Fetal Bovine Serum (FBS). In some embodiments, growth medium includes a high glucose DMEM. In some embodiments, the biocompatible carrier (e.g., growth medium) comprises one or more antibiotics.

In some embodiments, the kits are used for treating a subject having a defect in cartilage, bone, ligament, tendon, meniscus, or joint. In some embodiments, the kits are used for treating a subject having a degenerative defect or injury in cartilage, bone, ligament, tendon, meniscus, or joint. In some embodiments, the kits are used for treating a subject having osteoarthritis.

In some embodiments, a kit comprises a perforated osteochondral graft composition as described herein packaged in a container for storage and/or shipment. In some embodiments, the kit further comprises instructions for administering the composition.

In some embodiments, the kit further comprises biological adhesive components (e.g., fibrinogen and thrombin, for fibrin glue). In some embodiments, the perforated osteochondral graft composition and the biological adhesive components are packaged separately, and a user (e.g., a surgeon) adds the biological adhesive components to the surgery site prior to placement or implantation of the perforated osteochondral graft composition. In some embodiments, the perforated osteochondral graft composition is combined with the biological adhesive (e.g., fibrin glue) prior to packaging in the kit.

In some embodiments, the kit further comprises cells (e.g., stem cells). In some embodiments, the kit comprises biological adhesive and cells (e.g., stem cells), and the perforated osteochondral graft composition is combined with the biological adhesive prior to seeding the cells on the osteochondral graft.

VI. Examples

The following examples are offered to illustrate, but not to limit, the claimed invention.

Example 1

Laser Cutting to Generate Perforated Osteochondral Grafts

Osteochondral graft compositions were processed using an Epilog Zing 30 Watt CO2 engraving laser to cut a plurality of perforations into an osteochondral allograft (hemi-condyle allograft containing cartilage and bone). Table 1 shows the results of the tissue cutting experiments at varying speeds, powers, and frequencies.

TABLE 1

| Speed | 10% | 5% | 10% | 15% |
|---|---|---|---|---|
| Power | 100% | 100% | 65% | 35% |
| Frequency | 5000 Hz | 5000 Hz | 4000 Hz | 1500 Hz |
| Results | Cut through entire cartilage layer and several mm of bone | Cut through cartilage and several mm of bone | Cut through cartilage and subchondral bone | Cut through cartilage and subchondral bone |

Based at least in part upon these findings, it was determined that laser settings at 5-15% speed, 35-100% power, and 1500-5000 Hz frequency provide desirable results for producing perforated osteochondral allografts.

Example 2

Exemplary Perforated Osteochondral Grafts

FIGS. 1-6 depict exemplary perforated osteochondral grafts. As shown in FIG. 1, an osteochondral graft having a bone component and a cartilage component can be harvested from a cadaveric donor. The graft assembly can be treated according to any of the techniques described herein, so as to produce perforations (e.g., holes or microperforations) in the graft. The processed graft assembly can then be implanted in the recipient patient.

Figure 2:
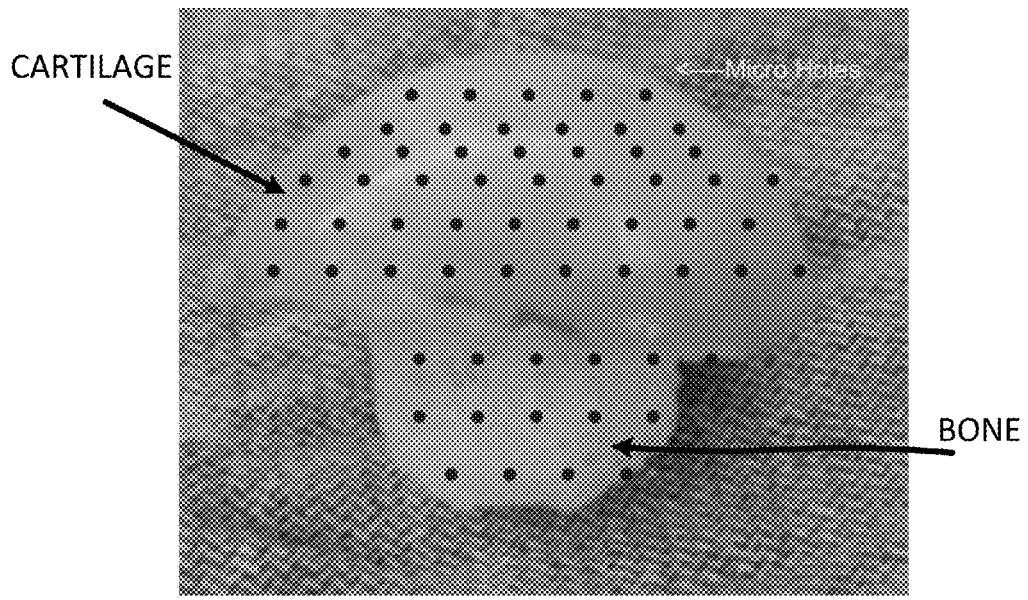
FIG. 2. An osteochondral graft can be processed to have multiple perforations ("micro holes") in the cartilage component as well as the bone component.

FIG. 2 depicts an osteochondral graft processed to have multiple micro-holes in the cartilage component as well as the bone component.

Figure 3:
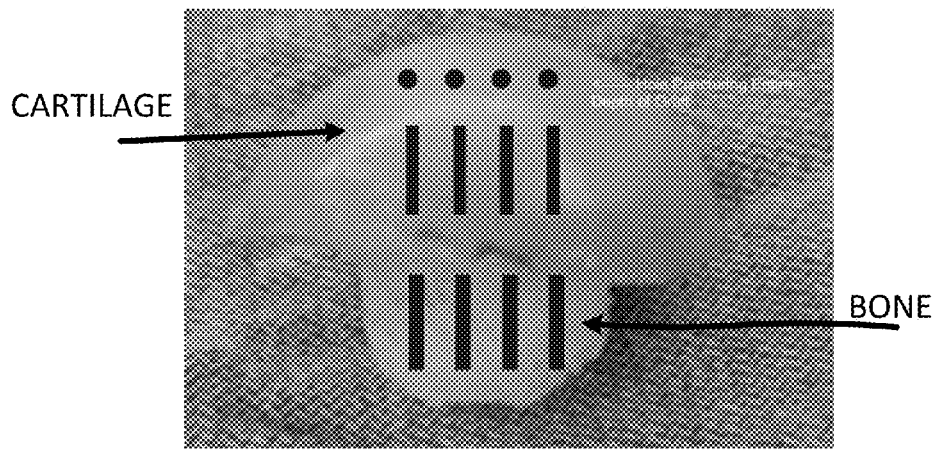
FIG. 3. An osteochondral graft can be processed to have multiple perforations in the cartilage component (upper set of bars) as well as the bone component (lower set of bars). The perforations can extend entirely through the depth of the graft, or partially to a depth within the graft.

FIG. 3 depicts an osteochondral graft processed to have multiple micro-holes in the cartilage component as well as the bone component. The holes can extend entirely through the depth of the graft, or partially to a depth within the graft.

Figure 4:
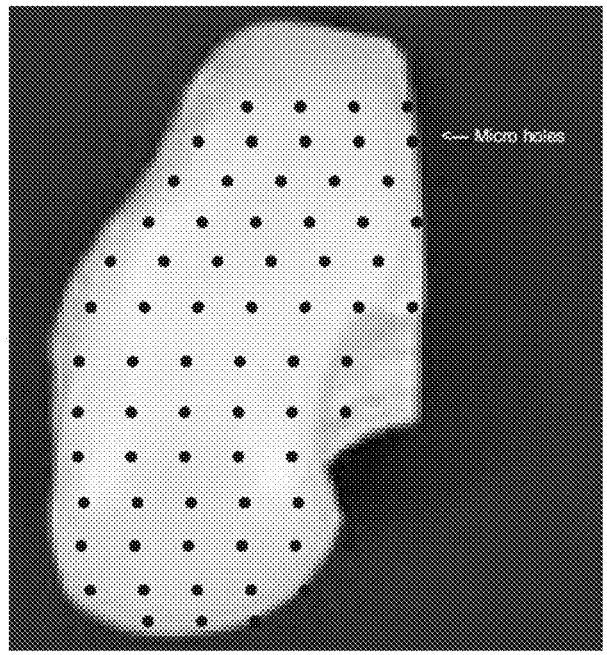
FIG. 4. An osteochondral graft can be processed to have multiple perforations ("micro holes") throughout the surface of the graft.

FIG. 4 depicts another osteochondral graft processed so that multiple micro-holes are formed in the graft.

Figure 5:
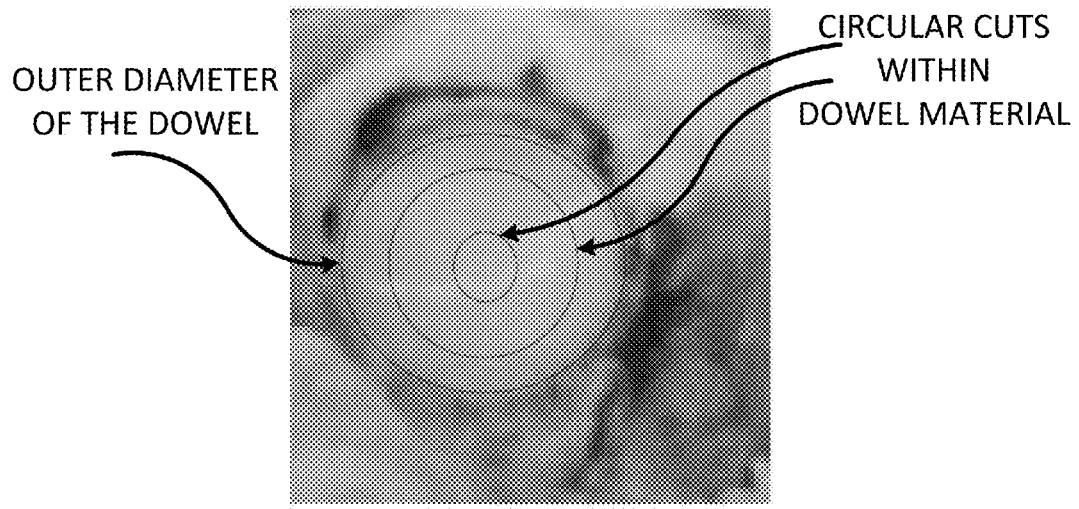
FIG. 5. An osteochondral graft embodiment in a dowel configuration comprising circular cut perforations. The outer circle represents the outer edge (circumference) of the dowel-shaped graft. The inner two circles represent circular cut perforations within the osteochondral tissue.

FIG. 5 depicts an osteochondral graft embodiment in a dowel configuration, which includes circular cut perforations. The outer circle represents the outer diameter of the dowel. The inner two circles represent circular cut perforations within the dowel material.

Figure 6A:
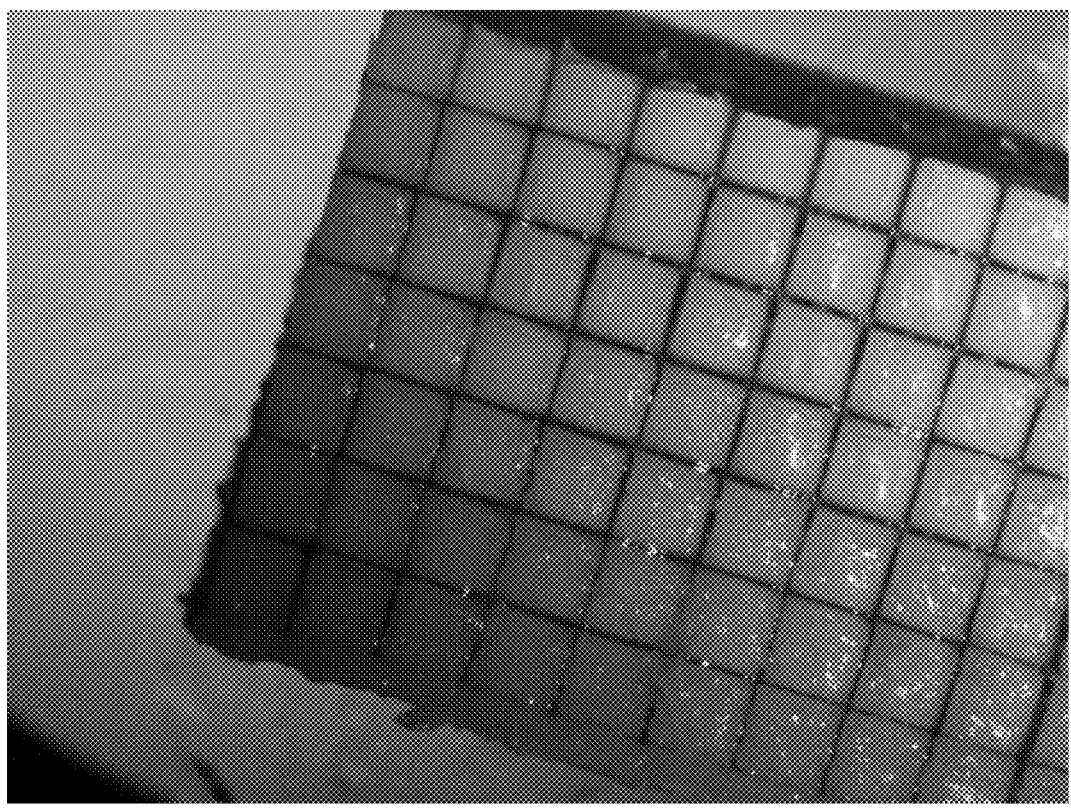
FIG. 6. Top view (A) and side view (B-C) of osteochondral tissue cut with a laser to produce perforations (microperforations) forming a grid pattern of lines. (B-C) 2× magnification (B) and 3× magnification (C) of a laser cut graft. The perforations extend partially through the depth of the osteochondral tissue. The blue arrow in (B) shows the subchondral bone layer.
Figure 6B:
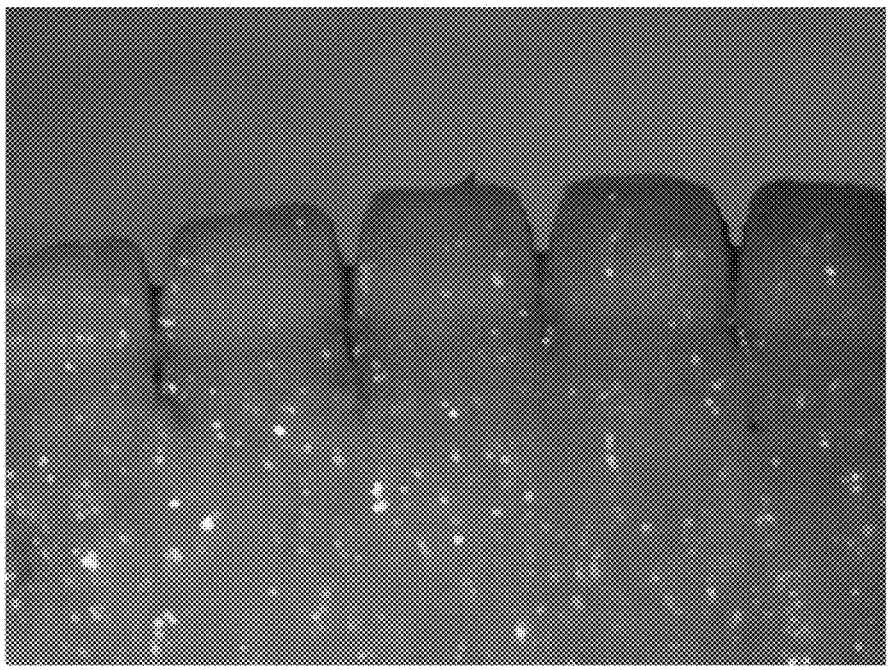
Figure 6C:
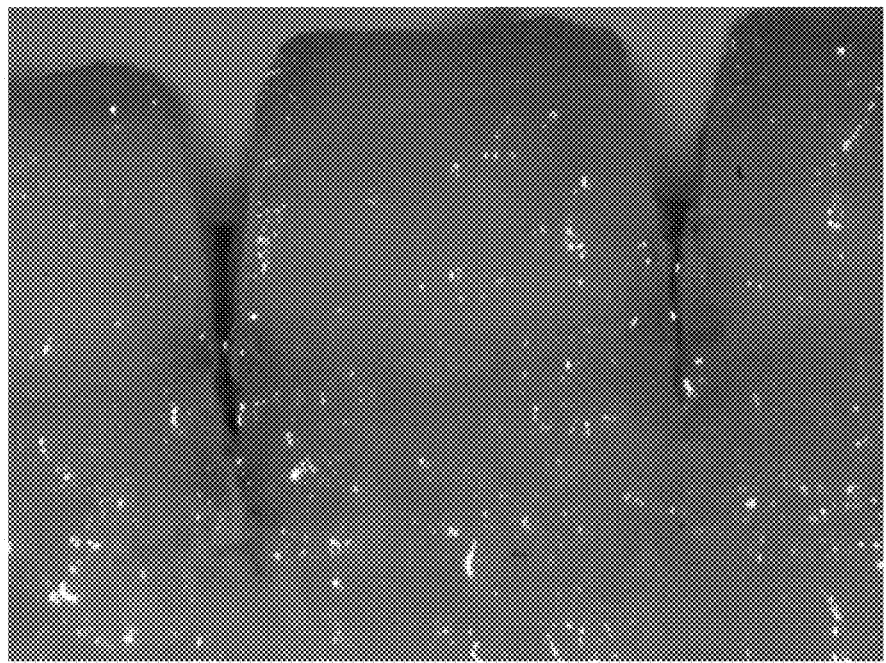

FIG. 6 depicts osteochondral tissue cut with a laser to produce perforations (microperforations) forming a grid pattern of lines. The perforations extend partially through the depth of the osteochondral tissue, through the cartilage portion of the osteochondral tissue and into the subchondral bone layer of the osteochondral tissue.

Although the foregoing invention has described in some detail by way of illustration and example for purposes of clarity of understanding, one of skill in the art will appreciate that certain changes and modifications may be practiced within the scope of the appended claims. In addition, each reference provided herein is incorporated by reference in its entirely to the same extent as if each reference was individually incorporated by reference.

What is claimed is:

1. A perforated osteochondral graft composition comprising a continuous portion of an osteochondral tissue containing native, viable chondrocyte cells from a donor of the osteochondral tissue, wherein the continuous portion of osteochondral tissue comprises a cartilage component and a bone component, and wherein the osteochondral graft composition comprises one or more perforations in the cartilage component, the bone component, or the cartilage component and the bone component.

2. The perforated osteochondral graft composition of claim 1, wherein the osteochondral tissue is harvested from a human cadaveric donor.

3. The perforated osteochondral graft composition of claim 1, wherein the one or more perforations have an average diameter from about 100 µm to about 3 mm.

4. The perforated osteochondral graft composition of claim 1, wherein the one or more perforations extend entirely through the depth of the continuous portion of osteochondral tissue.

5. The perforated osteochondral graft composition of claim 1, wherein the one or more perforations extend partially through the depth of the continuous portion of osteochondral tissue.

6. The perforated osteochondral graft composition of claim 1, wherein at least a portion of the surface of the perforated osteochondral graft composition is coated with a biological adhesive.

7. The perforated osteochondral graft composition of claim 1, wherein at least a portion of the surface of the perforated osteochondral graft composition is seeded with stem cells.

8. The perforated osteochondral graft composition of claim 7, wherein the stem cells are combined with a biological adhesive.

9. The perforated osteochondral graft composition of claim 1, wherein the perforated osteochondral graft composition is stored in a biocompatible medium.

10. The perforated osteochondral graft composition of claim 1, wherein the osteochondral graft composition comprises one or more perforations in the cartilage component.

11. The perforated osteochondral graft composition of claim 1, wherein the osteochondral graft composition comprises one or more perforations in the bone component.

12. The perforated osteochondral graft composition of claim 1, wherein the osteochondral graft composition comprises one or more perforations in the cartilage component and the bone component.

13. A method of treating a cartilage defect, a bone defect, or an osteochondtral defect in a subject, the method comprising administering to the subject at a cartilage defect, a bone defect, or an osteochondral defect a perforated osteochondral graft composition comprising a continuous portion of an osteochondral tissue containing native, viable chondrocyte cells from a donor of the osteochondral tissue, wherein the continuous portion of osteochondral tissue comprises a cartilage component and a bone component, and wherein the osteochondral graft composition comprises one or more perforations in the cartilage component, the bone component, or the cartilage component and the bone component.

14. The method of claim 13, wherein the osteochondral tissue is harvested from a human cadaveric donor.

15. The method of claim 13, wherein the one or more perforations have an average diameter from about 100 µm to about 3 mm.

16. The method of claim 13, wherein the one or more perforations extend entirely through the depth of the continuous portion of osteochondral tissue.

17. The method of claim 13, wherein the one or more perforations extend partially through the depth of the continuous portion of osteochondral tissue.

18. The method of claim 13, wherein at least a portion of the surface of the perforated osteochondral graft composition is coated with a biological adhesive.

19. The method of claim 13, wherein at least a portion of the surface of the perforated osteochondral graft composition is seeded with stem cells.

20. The method of claim 19, wherein the stem cells are combined with a biological adhesive.

21. The method of claim 13, wherein the osteochondral graft composition comprises one or more perforations in the cartilage component.

22. The method of claim 13, wherein the osteochondral graft composition comprises one or more perforations in the bone component.

23. The method of claim 13, wherein the osteochondral graft composition comprises one or more perforations in the cartilage component and the bone component.

24. The method of claim 13, wherein the method comprises treating a cartilage defect and administering the perforated osteochondral graft composition to a cartilage defect.

25. The method of claim 24, wherein the cartilage defect is a full-thickness articular cartilage defect.

26. The method of claim 13, wherein the method comprises treating a bone defect and administering the perforated osteochondral graft composition to a bone defect.

27. The method of claim 13, wherein the method comprises treating an osteochondral defect and administering the perforated osteochondral graft composition to an osteochondral defect.

* * * * *